US007138126B2

(12) United States Patent
Sansonetti et al.

(10) Patent No.: US 7,138,126 B2
(45) Date of Patent: *Nov. 21, 2006

(54) **TRANSFORMED *SHIGELLA***

(75) Inventors: Philippe Sansonetti, Paris (FR); Annick Fontaine, Paris (FR)

(73) Assignee: Institut Pasteur, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/814,589

(22) Filed: Apr. 1, 2004

(65) Prior Publication Data

US 2005/0031644 A1 Feb. 10, 2005

Related U.S. Application Data

(63) Continuation of application No. 08/466,698, filed on Jun. 6, 1995, now abandoned, and a continuation of application No. 08/118,100, filed on Sep. 8, 1993, now Pat. No. 5,762,941, which is a continuation of application No. 07/460,946, filed as application No. PCT/EP89/00831 on Jul. 14, 1989, now abandoned.

(30) Foreign Application Priority Data

Jul. 15, 1988 (EP) .................................. 88401842

(51) Int. Cl.
*A61K 39/02* (2006.01)
*C12N 1/00* (2006.01)
*C12N 1/36* (2006.01)

(52) U.S. Cl. ..................... 424/235.1; 435/243; 435/245

(58) Field of Classification Search .............. 424/235.1; 435/172.1, 243, 245
See application file for complete search history.

(56) References Cited

U.S. PATENT DOCUMENTS 5,762,941 A * 6/1998 Sansonetti et al. ....... 424/235.1

OTHER PUBLICATIONS

Bernardini et al., "Identification of icsA, A Plasmid Locus of *Shigella flexneri* that Governs Bacterial Intra- and Intercellular Spread Through Interaction with F-actin," *Proc. Nat. Acad., USA*, vol. 86, pp. 3867-3871 (1989).
Fontaine et al., "Role of Shiga Toxin in the Pathogenesis of Bacillary Dysentery, Studied by Using a Tox-Mutant of *Shigella dysenteriae 1*," *Infection and Immunity*, vol. 56, pp. 3099-3109 (1998).
Lawlor et al., "Aerobactin Genes in *Shigella* spp.," *J. of Bacterial.*, vol. 60, pp. 266-272 (1984).
Lett et al., "virG, a Plasmid-Coded Virgulence Gene of *Shigella flexneri*" Identification of the virG Protein and Determination of the Coding Sequence, *J. Bacterial.*, vol. 171, pp. 353-359 (1989).
Makino et al., "A Genetic Determinant Required for Continuous Reinfection of Adjacent Cells on Large Plasmid in *S. felxneri* 2a," *Cell*, 46, pp. 551-555 (1986).
Mills et al., "Analysis and Genetic Manipulation of *Shigella* Virulence Determinants for Vaccine Development", *Vaccine*, vol. 6, pp. 116-122 (1988).
Olsnes et al., "Isolation and Characterization of Shigella Shigae Cytotoxin," *J. Biol. Chem.*, vol. 255, pp. 284-289 (1980).
Ozenberger et al., "Genetic Organization of Multiple feb genes Encoding Ferric Enterobactin Transport Functions in *Escherichia coli*," *J. Bacteriol.*, 169, pp. 3635-3646 (1987).
Nassif et al., "Evaluation with an IUC:Tn10 Mutant of the Role of Aerobactin Production in the Virulence of *Shigella flexneri*," *Infection and Immunity*, vol. 55, pp. 1963-1969 (1987).
Newland et al., "Cloning of Shiga-Like Toxin Structural Genes from a Toxin Converting Phage of *Escherichia coli*," *Science*, vol. 230, pp. 179-181 (1985).
Payne et al., "Expression of Hydroxamate and Phenolate Siderophores by *Shigella flexneri*," *Chem Abstr.*, 99, 136626K (1983).
Sansonetti et al., "Multiplication of *Shigella flexneri* Within Hela Cells: Lysis of the Phagocytic Vacuole and Plasmid-Mediated Contact Hemolysis," *Infection and Immunity*, vol. 51, pp. 461-469 (1986).
Sansonetti et al., "OmpB (osmo-regulation) and icsA (cell-to-cell spread) Mutants of *Shigella flexneri*," *Vaccine*, vol. 9:416-21 (1991).
Seidah et al., "Complete Amino Acid Sequence of *Shigella* Toxin B-Chain," *J. Biol. Chem.*, vol. 261, pp. 13928-13931 (1986).

(Continued)

*Primary Examiner*—Mark Navarro
(74) *Attorney, Agent, or Firm*—Finnegan, Henderson, Farabow, Garrett & Dunner, L.L.P.

(57) ABSTRACT

A method for modifying a wild strain of an entero-invasive *Shigella* to produce a modified strain of *Shigella* that can be used for making a vaccine against the wild strain of *Shigella*. The genome of the wild strain of *Shigella* is transformed so that it cannot substantially invade cells of a human host and cannot spread substantially within infected cells and from infected to uninfected cells of the host and cannot produce toxins which will kill substantial numbers of the host's infected, as well as uninfected, cells. A first gene of the wild strain of *Shigella*, coding for a protein necessary for the *Shigella* to invade cells of the host, and a second gene, coding for a protein necessary for the *Shigella* to spread within infected cells and between the infected and uninfected cells of the host, are mutagenized.

39 Claims, 1 Drawing Sheet

OTHER PUBLICATIONS

Sekizaki et al., Localization of stx, a Determinant Essential for High-level Production of *Shiga* Toin by *Shiga* Toxin by *Shigella dysenteriae* Serotype 1, Near pyrF and Generation of stx Transposon Mutants, *Infection and Immunity*, vol. 55, pp. 2208-2214 (1987).

Strockbine et al., "Cloning and Sequencing of the Genes for *Shiga* Toxin from *Shigella dysenteriae* Type 1," *Chem. Abstr.*, vol. 109, pp. 67822g (1988).

Strockbine et al., "Cloning and Sequencing of the Genes for *Shiga* Toxin from *Shigella dysenteriae* Type 1," *J. Bacteriology*, 170: 1116-1122 (1988).

Timmis et al., "Localization of Shiga Toxin Gene in the Region of *Shigella dysenteria* 1, Chromosome Specifiying Virulence Functions," *FEMS Microbiology Letters*, vol. 30, pp. 301-305 (1985).

* cited by examiner

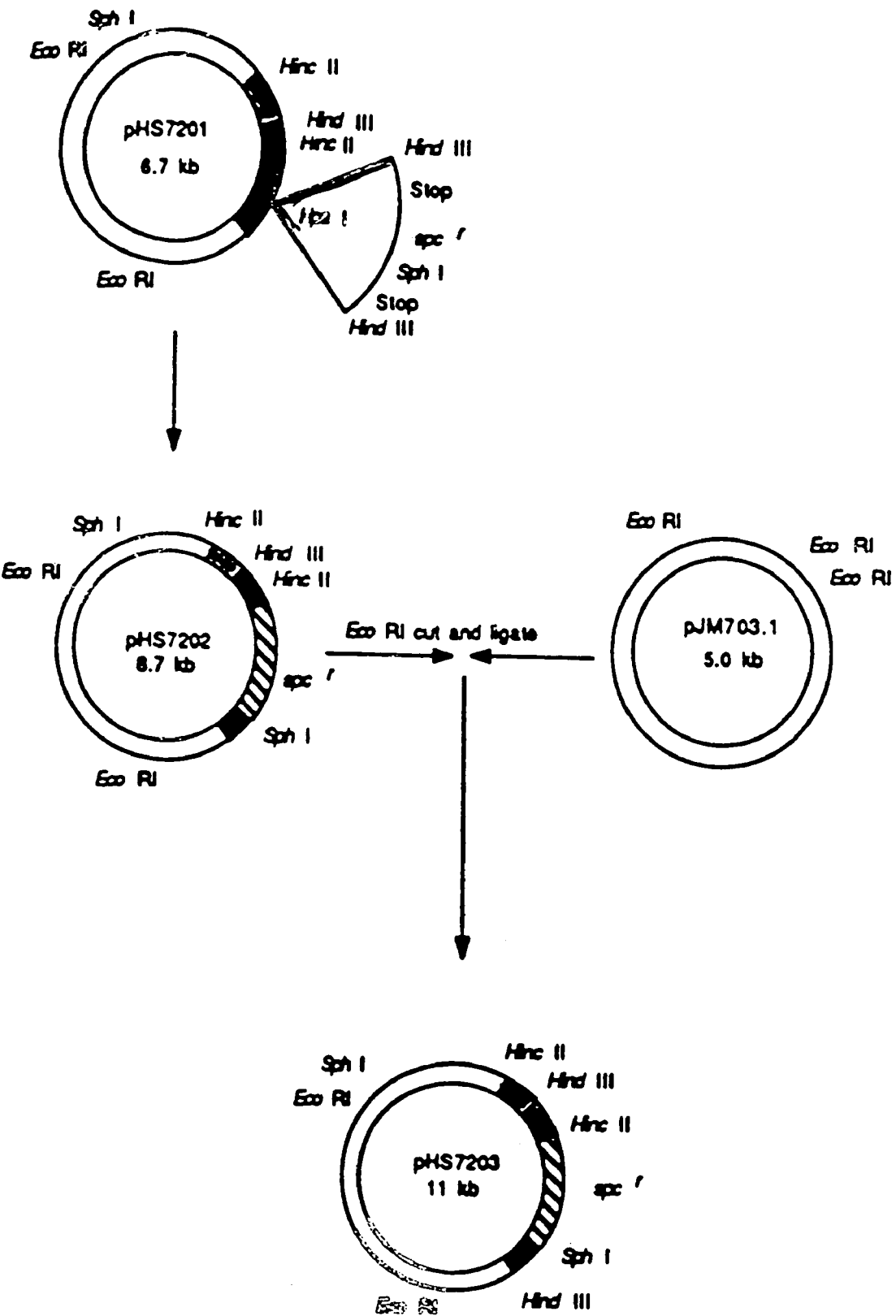

TRANSFORMED *SHIGELLA*

This is a continuation of application Ser. No. 08/466,698, filed Jun. 6, 1995 (abandoned), itself a continuation of application Ser. No. 08/118,100, filed Sep. 8, 1993 (Now U.S. Pat. No. 5,762,941), which is a continuation of application Ser. No. 07/460,946, filed Mar. 21, 1990 (abandoned), which is the national phase of PCT/EP89/00831, filed Jul. 14, 1989, published as WO90/00604, Jan. 25, 1990, all of which are incorporated herein by reference.

BACKGROUND OF THE INVENTION

This invention relates to a method of modifying the genome of an entero-invasive wild strain of *Shigella* so that the strain cannot substantially invade cells and tissues of an infected host and cannot spread substantially within infected cells and between infected and non-infected cells of the host and cannot produce toxins which will kill substantial numbers of the hosts' cells. This invention particularly relates to such a modified strain of *Shigella* which can be used to immunize a host against the wild strain of *Shigella*.

Shigellosis or bacillary dysentery is a disease that is endemic throughout the world. The disease presents a particularly serious public health problem in tropical regions and developing countries where *Shigella dysenteriae* 1 and *S. flexneri* predominate. In industrialized countries, the principal etiologic agent is *S. sonnei* although sporadic cases of shigellosis are encountered due to *S. flexneri*, *S. boydii* and certain entero-invasive *Escherichia coli*.

The primary step in the pathogenesis of bacillary dysentery is invasion of the human colonic mucosa by *Shigella* (23). Mucosal invasion encompasses several steps which include penetration of the bacteria into epithelial cells, intracellular multiplication, killing of host cells, and final spreading to adjacent cells and to connective tissue (9, 41, 55, 56). The overall process which is usually limited to the mucosal surface leads to a strong inflammatory reaction which is responsible for abscesses and ulcerations (23, 41, 55).

Even though dysentery is characteristic of shigellosis, it may be preceded by watery diarrhea. Diarrhea appears to be the result of disturbances in colonic reabsorption and increased jejunal secretion whereas dysentery is a purely colonic process (20, 41). Systemic manifestations may also be observed in the course of shigellosis, mainly in the cases due to *S. dysenteriae* 1. These include toxic megacolon, leukemoid reactions and hemolytic-uremic syndrome ("HUS"). The latter is a major cause of mortality from shigellosis in developing areas (11, 22, 38).

The role of Shiga-toxin produced at high level by *S. dysenteriae* 1 (6) and Shiga-like toxins ("SLT") produced at low level by *S. flexneri* and *S. sonnei* (19, 30) in the four major stages of shigellosis (i.e., invasion of individual epithelial cells, tissue invasion, diarrhea and systemic symptoms) is not well understood. For review see O'Brien and Holmes (32). Plasmids of 180–220 kilobases ("kb") are essential in all *Shigella* species for invasion of individual epithelial cells (41, 42, 44). This includes entry, intracellular multiplication and early killing of host cells (4, 5, 46). The role of Shiga-toxin and SLT at this stage is unclear. They do not appear to play a crucial role in intracellular multiplication and early killing (4, 12, 46). However none of the experiments which have been carried out has compared isogenic mutants in a relevant cell assay system. Recent evidence indicates that Shiga-toxin is cytotoxic for primary cultures of human colonic cells (27). Tissue invasion requires additional chromosomally encoded products among which are smooth lipopolysaccharides ("LPS") (44, 57), the non-characterized product of the Kcp locus (8, 44), and aerobactin (24, 28). A region of the *S. flexneri* chromosome necessary for fluid production in rabbit ileal loops has been localized to the rha-mtl regions and near the lysine decarboxylase locus (44). However, no evidence has been adduced to show that the ability to cause fluid accumulation is due to the SLT of *S. flexneri*. Thus, the role of Shiga-toxin in causing the systemic complications of shigellosis is still hypothetical. However, Shiga-toxin can mediate vascular damage since capillary lesions observed in HUS resemble those observed in cerebral vessels of animals injected with this toxin (1, 2, 22).

A mutant which lacks Shiga-toxin or SLT could indicate the role of these toxins in the disease process. *S. dysenteriae* 1, which produces the highest amount of this cytotoxin, could be transformed into such a Shiga-toxin negative mutant ("Tox−") and could serve best to indicate the role of the toxin—despite Sekizaki et al's (48) having obtained such a mutant which appeared as invasive in the HeLa cell assay and the Sereny test (49) as the wild strain. More importantly, such a Tox− mutant could be used to make a mutant which could not invade, and then multiply substantially within, cells of a host and also could not spread substantially within the host's infected cells and from there to the host's uninfected cells and also could not produce toxins which would kill subtantial numbers of infected, as well as uninfected, host cells. As a result, the Tox− mutant could be used to immunize a host against a wild strain of the *Shigella*.

SUMMARY OF THE INVENTION

A Tox− mutant of a wild strain of *S. dysenteriae* 1 is genetically engineered by allelic exchange with an in vitro mutagenized Shiga-toxin gene. The effect of this mutation in cell assay systems and animals shows that the mutant can be genetically engineered further to provide a mutant which cannot substantially invade and then spread within and between host cells and cannot produce Shiga-toxins in host cells.

Also in accordance with the invention, the Tox− mutant of the wild strain of *S. dysenteriae* 1 is genetically engineered further by allelic exchange with:

a) an in vitro mutagenized gene of *S. dysenteriae* 1 which encodes a protein necessary for *S. dysenteriae* 1 to invade a host's cells, as well as tissues, such as a gene which codes for a protein necessary for the chelation of iron and/or the transport of iron into *S. dysenteriae* 1 (e.g., an enterobactin or enterochelin gene of *S. dysenteriae* 1); and b) an in vitro mutagenized gene of *S. dysenteriae* 1 which encodes a protein necessary for *S. dysenteriae* 1 to spread within infected cells and between infected and uninfected cells, such as an intra-intercellular spread gene (e.g., an ics A or vir G gene).

Further in accordance with this invention, a mutant of a wild strain of *S. flexneri* is genetically engineered by allelic exchange with: a) an in vitro mutagenized gene of *S. flexneri* which encodes a protein necessary for *S. flexneri* to invade a host's cells, as well as tissues, such as a gene which codes for a protein necessary for the chelation of iron and/or the transport of iron into *S. flexneri* (e.g., an aerobactin gene of *S. flexneri*); and b) an in vitro mutagenized gene which encodes a protein necessary for *S. flexneri* to spread within and between the host's cells, such as an ics A gene.

Still further in accordance with this invention, the mutants of *Shigella* of this invention are used for making vaccines against the wild strains of *Shigella*.

BRIEF DESCRIPTION OF THE FIGURE

The Figure shows schematically the cloning of the Shiga-toxin operon and in vitro mutagenesis of the Shiga-toxin A subunit gene in Example 2. In plasmids pHS7201, pHS7202 and pHS7203 in the Figure: Solid lines indicate sequences from the A subunit gene; Stippled lines indicate B subunit gene sequences; and Stripped lines indicate sequences from the Ω insertion element.

DETAILED DESCRIPTION OF THE INVENTION

A method is provided for modifying a wild strain of an entero-invasive *Shigella* so that the modified strain can be used for making a vaccine against the wild strain of *Shigella*. The wild strain of *Shigella* is modified so that it cannot invade and then multiply substantially within infected cells of a host, particularly a human host, and cannot spread substantially within infected cells and from infected to uninfected cells of the host and cannot produce toxins which will kill substantial numbers of the host's infected, as well as uninfected, cells. The method involves transforming the genome, (e.g., the large virulence plasmid pHS7200) of the wild strain of *Shigella*, such as an *S. flexneri*, so that gene(s) of the wild strain, coding for one or more proteins necessary for the strain to invade an infected host's cells, as well as tissues (e.g., an aerobactin gene), and coding for one or more proteins necessary for the strain to spread within and between the infected host's cells (e.g., an ics A gene [60, 61]), are wholly or partly removed or permanently inactivated, preferably at least partly removed. For transforming the genome of a wild strain such as a *S. dysenteriae* 1, the method preferably involves also wholly or partly removing or permanently inactivating, preferably at least partly removing, the gene(s), preferably just the A subunit gene, coding for Shiga-toxin.

In the method of this invention, the genes of the wild strain of *Shigella* can be wholly or partly removed or permanently inactivated in a conventional manner, for example by allelic exchange with in vitro mutagenized genes, at least significant portions of which preferably have been removed. In this regard, it is preferred that the mutagenized genes not be simply inactivated by means of transposons which are inserted into the genes and which can be lost by the genes when they are reproduced in vivo in subsequent *Shigella* generations when making vaccines of this invention. Rather, the mutagenized genes preferably have had significant portions thereof deleted, and suitable vaccine-compatible marker genes are preferably inserted within such deletions. Such marker genes permit so-transformed *Shigella* to be easily identified. The preferred marker genes are the heavy metal-resistance genes such as the mercury, arsenate, arsenite, antimony, cadmium, zinc and/or cobalt-resistance genes (62, 63, 64, 65).

The cells of the modified strain can be cultured and then attenuated in a conventional manner. The cells can then be mixed with conventional pharmaceutically acceptable vehicles (e.g., an aqueous saline solution) and optionally with conventional excipients (e.g., a pharmaceutically acceptable detergent) to form a vaccine against the wild strain. The vaccine can be formulated to contain a final concentration of cell material in the range of 0.2 to 5 mg/ml, preferably 0.5 to 2 mg/ml. After formulation, the vaccine can be incorporated into a sterile container which is then sealed and stored at a low temperature (e.g., 4° C.), or it can be freeze dried.

In order to induce immunity in a human host to a wild strain of *Shigella*, one or more doses of the vaccine, suitably formulated, can be administered in doses containing about $10^9$–$10^{11}$ lyophilized *Shigella* cells. The vaccine can be administered orally in a conventional manner. The treatment can consist of a single dose of vaccine or a plurality of doses over a period of time.

The Examples, which follow, illustrate this invention.

EXAMPLES

Unless otherwise indicated, the cloning and transformation procedures and techniques used in the Examples are the same as are generally described in Maniatis et al, "Molecular Cloning—A Laboratory Manual", Cold Spring Harbor Laboratory (1982).

The strains, used in Example 1–6, and their phage or plasmid content are set forth in Table I.

Two media were used in the Examples: M9 minimal medium ($Na_2HPO_4.12H_2O$: 15 g/l, $KH_2PO_4$: 3 g/l, NaCl: 0.5 g/l, $NH_4Cl$: 1 g/l, $MgSO_4.7H_2O$: 0.05 g/l) and Trypto Casein Soja Broth (Diagnostics Pasteur, Marnes la Coquette, France).

Example 1

Cloning of the Shiga-Toxin Operon

Total DNA was prepared (50) from a wild type antibiotic-sensitive *S. dysenteriae* 1 strain SC500 obtained from Centre National de Référence des Shigelles of Institut Pasteur, Paris, France. 10 μg of DNA were digested with EcoRI (Amersham, Buckinghamshire, UK) and loaded on a 0.7% agarose gel. Fragments ranging from 3.5 to 4.5 kb were electroeluted. 0.1 μg of purified fragments was ligated to 1 μg of cos-ligated, EcoRI cut, dephosphorylated λ GT11 arms (Stratagene Cloning System, San Diego, USA) and packaged using Packagene System (Progema Biotec, Madison, USA) according to the suppliers recommendations. The packaged DNA was then transfected into *E. coli* Y1090(59). The λ GT11 bank was then screened with 13C4, a monoclonal antibody specific for the B subunit of SLT1 (54) obtained from A. D. O'Brien, U.S.U.S.H., Bethesda, Md., USA. $10^3$ recombinant phages were plated on Y1090 in LB soft agar. Plates were incubated at 37° C. for 12 hours. A nitrocellulose filter (Schleicher and Schüll, Dassel, FRG), previously dipped into a 10 mM isopropylthiogalactoside ("IPTG") solution (Sigma, St Louis, Mo., USA) was applied to the plate which was then incubated at 42° C. for 2.5 hours. The filter was removed from the plate and incubated 1 hour at 37° C. in PBS-milk (50 g/l dehydrated low-fat milk in 1×PBS), washed five times with 1×PBS, and incubated for 1 hour with the 13C4 monoclonal antibody in its non-diluted hybridoma cell supernatant. After five washes in PBS-milk, the filter was incubated 1 hour at 37° C. in PBS-milk containing a 1/200 dilution of sheep anti-mouse IgG antibody conjugated with alkaline phosphatase (Biosys, Compiègne, France). The filter was washed again in 1×PBS and placed in the staining solution: 0.33 mg/l nitro-blue tetrazolium, 0.16 mg/l 5-bromo-4-chloro-3-indolyl phosphate (both compounds from Sigma), 100 mM Tris HCl pH 9.5, 100 mM NaCl, 50 mM $MgCl_2$. Positive clones were plaque purified and transfected into Y1089 (59). DNA was then prepared from the lysogen (13). Subcloning was done in the EcoRI site of plasmid vector pUC8 in *E. coli* JM83 (58). Subclones of *E. coli* JM83 were tested with monoclonal antibody 13C4 as described above with the following modifications: a dry nitrocellulose filter was applied onto the plate and 2 ml of a 2 mg/l polymyxin B solution in PBS were added on top of the filter. The plate was then incubated at 37° C. for 45 minutes before starting PBS-milk incubation. Subclone pHS7201 in *E. coli* JM83, containing the B subunit of SLT1, was identified.

Subclone pHS7201 of *E. coli* JM83 was found to have a stronger signal in colony immunoblot assay in the presence of 13C4 monoclonal antibody than parental strain SC500 due to the gene dosage effect. A restriction map of the Shiga-toxin coding region within pHS7201 was identical to that of SLT1 (14). The A subunit gene was seen to possess a unique HpaI site located 310 bp downstream from the ATG starting codon where a cassette could be inserted as described in Example 2.

Example 2

In vitro Mutagenesis of the Shiga-Toxin A Subunit Gene

In subclone pHS7201, the entire Shiga-toxin operon is contained in a 4.2 kb EcoRI DNA fragment. In vitro mutagenesis of the A subunit gene was done,by inserting the interposon $\Omega(37)$ which codes for spectinomycin resistance and is flanked on each side by T4 translation transcription stop-signals. $\Omega$ was purified as an HindIII 2 kb fragment, and its ends were filled in by the Klenow fragment of DNA polymerase I. $\Omega$ was then ligated to HpaI linearized pHS7201 to generate the recombinant plasmid pHS7202 as shown in the Figure. The 6.2 kb EcoRI fragment containing the mutagenized sequence was then purified and ligated with the EcoRI site of the suicide plasmid vector pJM703.1 (51) to generate recombinant plasmid pHS7203 as shown in the Figure. pJM703.1 replicates only if its deficient R6K origin is complemented in-trans by the pir function contained in the lambda phage integrated in the genome of *E. coli* SM10 (21). This strain also contains the transfer genes of the broad host range IncP-type plasmid RP4 integrated in its chromosome. pJM703.1 can thus be mobilized by SM10 λ pir (21) because it contains the Mob site from RP4 (51). pHS7203 was thus stably maintained in strain SM10 λ pir and was then conjugally transferred into wild type *S. dysenteriae* 1 strain SC500. Matings were performed on cellophane membranes, selection was obtained by plating on M9 minimal medium supplemented with thiamine, methionine, tryptophan and nicotinic acid at a concentration of 10 μg/ml each, 0.2% glucose and 50 μg/ml spectinomycin. Colonies growing on selective medium were purified and identified as *S. dysenteriae* 1 by agglutination with a specific rabbit antiserum (Diagnostics Pasteur).

Allelic exchange between the wild-type chromosomal Shiga-toxin gene and the in vitro mutagenized gene of Shiga-toxin was shown by colony blot immunoassay, using the monoclonal antibody 13C4 to detect *S. dysenteriae* 1 cells expressing a Tox-phenotype.

The presence of the Tox⁻ modification in the genomes of the *S. dysenteriae* 1 cells was verified with a probe made from the 655 bp HindIII-HincII fragment containing part of the A subunit gene and the entire B subunit gene from the 4.2 kb EcoRI fragment, described above, containing the entire Shiga-toxin operon. The 2 kb HindIII fragment, described above, containing the $\Omega$ interposon, was also used as a probe (37). The DNA fragments, used as the probes, were labeled by nick-translation (39) with $^{32}$p-labeled 5'-dCTP (Amersham). Total DNA was prepared from two Tox-clones and analyzed by hybridization with the Shiga-toxin probe and the $\Omega$ probe. The DNA fragments were transferred from agarose gels to nitrocellulose filters (Schleicher and Schüll) by the method of Southern (53). Hybridization was carried out at 65° C. overnight, and washing was done at 65° C. in 6×SSC. The probes showed that the 4.2 kb EcoRI fragment from *S. dysenteriae* 1 containing the toxin genes had been replaced in the Tox-mutants by the 6.2 kb fragment, which hybridized with both probes. This result showed that the flanking regions on each side of the mutagenized toxin gene in pHS7203 had recombined with their counterparts in the SC500 genome, thus replacing the wild-type A subunit gene by the mutated gene.

One of these Tox-clones, SC501, was selected for further study, and clone SC501 was deposited with the Centre Nationale de Cultures de Microorganismes of Institut Pasteur, Paris, France, under accession no. I-774, on Jun. 30, 1988.

Example 3

Assays of Cytotoxicity, Growth within HeLa Cells, Macrophage Detachment and Toxicity in Rabbit Ileal Loop and in Monkey SC500 and SC501, as well as their non-invasive derivatives SC502 and SC503 respectively (obtained by the spontaneous-cure (i.e., loss) of their large virulence plasmid pHS7200 which is necessary for invasion of cells), were grown for 48 hours in 200 ml of iron-depleted medium. Glassware was pretreated with 6N HCl and rinsed extensively with iron free $H_2O$. The medium contained M9 salts supplemented with 15 μg/ml $CaCl_2$, 5 mg/ml casaminoacids, 2 mg/ml glucose, 50 μg/ml thiamine, 20 μg/ml L-tryptophane, 10 μg/ml nicotinic acid and 150 μg/ml human transferrin (Sigma). The bacteria were washed twice in saline and resuspended in 3 ml of PBS. Lysozyme was added at a final concentration of 0.2 mg/ml. After a 30 minute-incubation at room temperature (25° C.), 30 μl EDTA 0.5 M pH8 was added, and the cells were transferred to an ice bath and sonicated. Sonic extracts were filter-sterilized and kept frozen at −20° C. Filter sterilized culture supernatants and bacterial extracts were assayed for cytotoxicity on HeLa cells grown in minimal essential medium with Earle's salts and N-glutamine (Gibco, Paisley, Scotland, UK) supplemented with 10% foetal calf serum (Gibco). Serial dilutions were made in cell culture medium (100 μl) in a microtitier plate. Each well was inoculated with $2 \times 10^4$ cells in 100 μl. Plates were then incubated at 37° C. in 5% $CO_2$ for 24 hours. Neutralization assays were performed both with a rabbit polyclonal serum and the 13C4 monoclonal antibody. Plates were examined under light phase microscopy, then stained with Giemsa. Cytotoxicity was calculated as the cytotoxic dose 50% (CD50) per mg of protein of the extract.

Multiplication of bacteria within HeLa cells was assayed (46). Non-confluent monolayers of HeLa cells in 35 mm plastic tissue culture dishes (Becton Dickinson Labware, Oxnard, Calif., USA) were inoculated with bacteria, resuspended in 2 ml of minimum essential medium ("MEM", Gibco) at a multiple of infection ("MDI") of 100, centrifuged for 10 minutes at 2,200×g and incubated for 30 minutes at 37° C. to allow entry. Plates were then washed three times with Earle's Balanced Salt Solution ("EBBS", Gibco) and covered with 2 ml of MEM with gentamicin (25

μg/ml). This was defined as time 0 (To). After one hour of incubation at 37° C., preparations were washed again, with EBSS and covered with 2 ml of MEM without antibiotic (T1). Incubation was continued for three more hours (T1–T4). Two plates were removed every hour. One plate was washed three times with EBSS and Giemsa stained to calculate the percentage of infected HeLa cells. The other was washed five times with EBSS to eliminate viable extracellular bacteria. Cells were trypsinized, counted and lysed at 0.5% sodium deoxycholate in distilled water. Dilutions were plated onto Trypticase Soy Agar. The average number of bacteria per infected HeLa cell was calculated. Experiments were repeated four times. Intracellular growth curves were drawn and the slope at exponentional phase was calculated.

Assay for macrophage detachment and killing was performed (4) using J774 macrophages (52) maintained in RPMI 1640 (Flow Laboratories Inc., McLean, Va., USA) supplemented with complement-inactivated foetal calf serum (Gibco) and 2 mM glutamine (Gibco). Eighteen hours before infection, $7 \times 10^5$ macrophages in 35 mm plastic tissue culture dishes (Becton Dickinson Labware) were labeled in a culture medium. containing 0.5 μCi of [$^3$H] uridine per ml (Amersham). Cells were washed three times with EBSS before addition of 1 ml of the bacterial suspension in RPMI 1640 at a MOI of 100. Infection was performed for one hour at 37° C. in 5% $CO_2$. Monolayers were then washed three times with EBSS (To) and covered for one hour at 37° C. in 5% $CO_2$ with 2 ml of RPMI supplemented with 2 mM glutamine and gentamicin 25 μg/ml (T1). Plates were then washed three times with EBSS and incubated in 5% $CO_2$ for 3 more hours (T1–T4) at 37° C. in RPMI glucose without gentamicin. Two plates were removed every hour, cultures were washed three times with EBSS and the percentage of non viable macrophages among cells that still adhered to the plastic surface was determined by trypan blue staining. The percentage of residual macrophages was then determined by measuring the amount of radioactivity remaining in the dish. Adherent cells were lysed with 1 ml of 0.5% sodium deoxycholate in distilled water and 100 μl of this lysate was precipitated and counted (4).

Rabbit ligated ileal loops of 10 cm were prepared in rabbits of ca. 2 kg which were anesthesized with 0.5 ml/kg of 6% sodium pentobarbital. Inocula of $10^7$ and $10^9$ CFU in 1 ml of Trypticase Soy Broth were tested. Rabbits were sacrificed 18 hours later. Fluid accumulation within loops was recorded, and the volume-to-length ration ("V/L") was calculated. Portions of infected loops were fixed in 10% buffered formalin. Specimens were processed by standard procedures and stained with hematoxylin-eosin-safranin.

Eight rhesus monkeys weighing 3.5 to 4.5 kg were injected intramascularly with 50 mg of ketamine chlorhydrate (Imalgene 500, Rhône Mérieux, Lyon, France). Each animal was inoculated intragastrically with $1.5 \times 10^{11}$ of SC500 and SC501 microorganisms resuspended in 20 ml of Trypticase Soy Broth and 14 g/l sodium bicarbonate (50/50). Plating of the inoculum on Congo-red agar indicated that less than 1% of the bacteria in the inoculum had lost their invasive property (26). Stools were examined daily for diarrhea, presence of pus, mucus and blood. Intensity of each of these symptoms was graded from 0 to 3+ every day. For each animal, the severity of a given symptom was expressed as an index which represented a sum of the accumulated "+" for each symptom. Immediate autopsy was performed in monkeys who died of fulminant dysentery. Species ware processed as described above for rabbit tissues.

Results

SM10 λ pir (pHS7203) was noncytotoxic in the cytotoxicity assay. After conjugative transfer of pHS7203 into S. dysenteriae, clones that displayed the $Amp^S$ $Spc^R$ phenotype were tested in the colony immunoblot assay. Five per cent displayed a Tox⁻ phenotype. SC501 showed a cytotoxicity of 347 CD50/mg of protein, which was the same order of magnitude as that of well-known *E. coli* K12 (412 CD50/mg). Residual cytotoxicity from SC501 could not be neutralized by an anti-Shiga-toxin polyclonal serum.

The presence of the Tox-mutation in strain SC501 did not significantly alter its capacity to grow intracellularly within HeLa cells since its rate of exponential growth, expressed in generations/hour, was 2.6±0.7 compared to 2.5±0.6 for wild-type strain SC500. In addition, no significant difference could be observed in the efficiency of rapid killing of J774 macrophages by SC500 and SC501. Both cell detachment and appearance of Trypan Blue positive cells progressed at similar rates over four hours, thus indicating that Shiga-toxin released within infected cells neither significantly affected the rate of intracellular growth nor increased rapid killing of host cells.

The effect of the $Inv^-$ and $Tox^-$ mutations on the pathogenicity of *S. dysenteriae* 1 in the rabbit ligated loop model was determined by the effect on fluid production within loops. Mean and standard deviations were computed from the results obtained in six loops for each strain at either of the two inocula (i.e., $10^9$ and $10^7$ CFU). For invasive strains (i.e., SC500, $Inv^+$, $Tox^+$ and SC501, $Inv^+$, $Tox^-$) at both inocula, the lack of Shiga-toxin production decreased fluid accumulation, but the difference was not statistically significant, indicating that invasion and subsequent inflammation are primarily responsible for fluid accumulation. For non-invasive strains (i.e., SC503, $Tox^+$ and SC502, $Tox^-$) a striking difference was observed since only the strain producing Shiga-toxin elicited fluid accumulation. This indicated that, in the rabbit model, Shiga-toxin is the only enterotoxin of *S. dysenteriae* 1, whatever the role this enterotoxin may play in the course of the disease. Histopathological studies showed severe lesions including abscesses and ulcerations destroying numerous villi at both inocula either with SC500 or SC501. In general, lesions were more severe in loops infected with the wild-type strain, but the observation that the difference was minor indicated that invasion was the major factor of pathogenecity.

Loops infected with SC502, the non-invasive $Tox^+$ strain, were severely altered with swelling and shortening of the villi, oedema and inflammation of the lamina propria, alterations of epithelial cells with large amounts of mucus shed from goblet cells and areas of killed enterocytes with pycnotic nuclei. However, the most striking feature was hemorrhages throughout the epithelial layer.

The effect of the $Tox^-$ mutation on the pathogenicity of *S. dysenteriae* 1 was shown in monkeys. Two animals died of fulminant dysentery at day 4 in both the group injected with SC500 and the group injected with SC501, each group thus indicating that Shiga-toxin was not required for lethal dysentery. No significant differences could be observed in the volume of diarrheic stools and the amount of pus and mucus, although the latter were difficult to quantify with precision. On the other hand, the presence of blood was a constant characteristic of abnormal stools in animals infected with SC500 whereas only one animal infected with SC501 showed transcient presence of a slight amount of blood. Autopsies performed immediately after the death of the animals showed obvious differences in the colonic peritoneal mesothelium which was particularly apparent on the surface of the sigmoid on which patchy hemorrhagic areas could be observed only in the case of animals infected with SC500. On the average, the number and severity of abscesses was similar, but purulent necrosis of the mucosa with destruction in Lieberkühn glands was only observed, in some areas, in animals infected with SC500. Inflammatory infiltration of the chorion, submucosal tissues and peritoneum was also more severe in these animals. In addition, the inflammatory infiltrate of the peritoneal mesothelium which was characteristic of animals infected with SC500 as compared to SC501, was predominantly perivascular thus confirming the gross examination which suggested the presence of a severe peritoneal vasculitis. However, the most striking difference was observed at the level of the capillary circulation within the interglandular chorion. Monkeys infected with SC500 showed hemorrhages disrupting the structure of the upper part of the mucosa. Erythrocytes could be observed being released into the intestinal luman through microabscesses which caused local interruption of the epithelial lining. These hemorrhages were obviously due to destruction of the capillary loops. On the other hand, monkeys infected with SC501 showed dilatation of the capillary loop but no disruption. White blood cell counts performed before and at day 3 after infection showed: at day 0, no significant difference in polymorpho nuclear cell ("PMN") counts, and myelemia was absent; and at day 3, the drop in blood PMN and the level of myelemia were each more pronounced in monkeys infected by SC500.

Conclusions

Circumstantial evidence in humans supports the hypothesis that Shiga-toxin is a true virulence factor. Volunteers fed strain 725, an invasive, low-toxin producing, chlorate-resistant mutant of *S. dysenteriae* 1, showed less severe symptoms than those fed the wild-type strain M131 (25). Patients experiencing natural infection usually develop more severe symptoms including HUS when infected with *S. dysenteriae* 1 than with other *Shigella* serotypes (7). They rapidly develop toxin-neutralizing antibodies (18).

The Tox$^-$ mutant of *S. dysenteriae* 1, SC501, has been shown to produce a residual amount of cytotoxin similar to *E. coli* K12. This mutant has been used to study the role of this Shiga-toxin in the virulence of *S. dysenteriae* 1. Cellular assays and more definitive animal models have been used.

Assays using HeLa cells and J774 macrophages in monolayers have shown that secretion of Shiga-toxin did not affect the rate of exponential growth within infected cells as suggested for SLT in *S. flexneri* in a previous study (46). These results were in agreement with the observation that two other low toxin producer mutants (25, 48) as well as the SC501 mutant do not affect keratoconjuctivitis (49) which is known to correlate with the capacity of bacteria to multiply within an epithelium (35). As also suggested previously (4, 12), no correlation could be observed between Shiga-toxin production and early killing of host cells. Although such data need confirmation in assays that would more closely mimic the actual infection, they certainly indicate that Shiga-toxin does not play a major role at the intracellular stage of infection. Invasion appears to trigger early metabolic events which mediate killing of host cells (47) more rapidly than the slow acting process of Shiga-toxin (12).

Infection of rabbit ligated intestinal loops demonstrated only slight differences in the severity of mucosal lesions after 18 hours with both the SC500 and SC 501 inocula. However, the duration of exposure and closing of loops may mask the effect of cytotoxin production and make invasion the primary event. Results concerning enterotoxicity were more difficult to analyze in the case of invasive bacteria since the amount of fluid produced, although lower at both inocula for the Tox$^-$ mutant, was not significantly different from that. elicited by the wild-type strain. This indicated that invasion of tissues is sufficient to block the reabsorbative functions of the epithelium. On the other hand, the striking difference observed between non-invasive Tox$^+$ and Tox$^-$ mutants indicates that, within the limits of sensitivity of the rabbit model, Shiga-toxin is the only enterotoxin of *S. dysenteriae* 1. This is in agreement with previous studies (16, 17, 33). However, when observing fluid production by Inv$^+$ and Inv$^-$ mutants, the nature of the fluid produced varies according to the infecting strain. Invasive strains elicit production of a viscous, mucopurulent, sometimes bloody liquid which probably reflects the extent of abscesses ulcerated within the lumen regardless of the amount of Shiga-toxin produced, whereas non-invasive, Tox$^+$ strains produce a watery, sometimes bloody, liquid which is more a reflection of enterotoxicity and cytotoxicity. Histopathological studies of tissue samples from loops infected with SC502, the Inv$^-$, Tox$^+$ mutant, showed an important inflammatory infiltrate of the lamina propria and major alterations predominantly at the tip of shortened villi. This confirmed the cytotoxicity of Shiga-toxin on enterocytes in vivo (27). However, the most striking feature was infiltration of the epithelial lining by erythrocytes which were shed into the lumen along with important amounts of mucus. This observation, which suggested that major vascular alterations had occurred within the lamina propria, was subsequently confirmed in the monkey model.

Intragastric inoculation of SC500 and SC501 in macaque monkeys demonstrated that lethal fulminant dysentery could occur regardless of Shiga-toxin production. No significant difference was observed in the amount of diarrhea, pus and mucus in stolls. Absence of watery diarrhea and equal amount of stool were not consistent with previous studies suggesting increased jejunal secretion bu Shiga-toxin (41). The only striking difference was the presence of blood in dysenteric stools of animals infected with the wild type strain. A recent paper reported that, among patients presenting shigellosis, those who eliminated strains of higher cytotoxicity were more likely to present blood in their stools (36). Histopathological observations confirmed the presence of vascular damages which appeared particularly characteristic in the sigmoid since monkeys infected with the wild type strain showed total destruction of the capillary loops within the chorion whereas the vascular system of animals infected with the Tox$^-$ mutant showed turgescent but mostly intact vessels. This certainly explains the presence of bloody stools in the former group. In addition, observation of the peritoneal mesothelium showed oedema and severe inflammatory vasculitis. Thus, release of Shiga-toxin by invading bacteria within the tissues may locally enhance severity of the mucosal lesion by evoking local ischemia through destruction of the chorion blood flow and alterations of the peritoneal as well as possibly mesenteric circulation. This effect appears to be local or loco-regional since observation of kidney tissues did not show evidence of capillary vasculitis at this stage of the disease (data not shown). Such vascular alterations may be consistent with observations in hemorrhagic colitis due to *E. Coli* 0157:H7 (40) in which a radiologic aspect of ischemic colitis has been described (34). These strains produce high levels of SLT1 (31) which has a direct cytopathic effect on dividing endothelial cells (15).

Another difference observed between animals infected with Tox$^+$ and Tox$^-$ strains was the severity of mucosal inflammation and subsequent abscesses. In many areas of the sigmoid and transverse colons, lesions appeared of similar intensity, but only animals infected with SC500 showed areas with impressive purulent destruction of mucosal tissues.

Higher intensity of the purulent exsudate was reflected in a more dramatic drop of blood PMN with consecutive myelemia at day three of infection. It is believed that, in addition to the marrow and vascular compartments, a third PMN compartment is opened at the colonic level during shigellosis. Shiga-toxin is expected to increase the number of PMN entrapped within this new compartment through vascular alterations which increase diapedesis as well as direct release of PMN within mucosal tissues. This would account for the rapid and severe granulocytopenia observed in animals infected by the wild type strain and for subsequent higher myelemia which may be an equivalent of the leukemoid reaction sometimes observed in the course of severe shigellosis. Such a model does not postulate a systemic effect of Shiga-toxin.

The foregoing results thus suggest that Shiga-toxin plays a limited role when released intracellularly within epithelial and phagocytic cells. However, Shiga-toxin released within infected tissues appears to act predominantly through intestinal vascular damage.

Example 4

Using the procedure of Example 2, SC501 is genetically engineered by in vitro mutagenesis of its operon coding for enterochelin. The suicide plasmid vector pJM703.1, that is utilized, contains the enterochelin operon of *S. dysenteriae* 1, with each of its ent F, Fep E, Fep C and Fep D subunit genes mutagenized with an interposon which codes for resistance to the herbicide Biolafos and a suitable promoter for the herbicide resistance gene. The resulting clone, SC504, is Tox$^-$ and enterochelin$^-$ ("Ent$^-$").

Example 5

Using the procedure of Example 2, SC504 is genetically engineered by in vitro mutagenesis of its ics A gene. The suicide plasmid vector pJM703.1, that is used, contains the ics A gene of *S. flexneri* (60, 61), which has been mutagenized with an interposon. The resulting clone, SC505, is Tox$^-$, Ent$^-$ and ics A$^-$ and can be used in making a vaccine against *S. dysenteriae* 1.

Example 6

Using the procedure of Example 2, a wild type *S. flexneri* is genetically engineered by in vitro mutagenesis of its gene coding for aerobactin and its ics A gene. The suicide plasmid vector, that is used, contains the aerobactin and ics A genes of *S. flexneri* which have each been mutagenized with an interposon. The resulting clone, SC506, is aerobactin$^-$ and ics A$^-$ and can be used in making a vaccine against *S. flexneri*.

Example 7

Using the procedure of Examples 1, 2 and 4, a 400 basepair Bal31 deletion is made, starting from the unique Hpa1 site, inside the A subunit gene of the Shiga-toxin operon in a DNA fragment from *S. dysenteriae* 1 in strain SC500. The resulting fragment is religated with a 257 basepair fragment containing the P1 promoter of pBR322, thus allowing high expression of the B subunit protein. This fragment, containing the mutagenized toxin A gene, is cloned into a conditional suicide vector which contains a replication of origin under the control of the *E. coli* lac promoter and a kanamycin resistance gene. In *S. dysenteriae* 1, this vector will replicate only if IPTG is present in the culture medium. A mercury-resistance cartridge (65) is inserted upstream from the mutagenized A subunit gene. The resulting plasmid is transformed into the wild type *S. dysenteriae* 1 strain SC500 in the presence of IPTG. Colonies of the resulting *Shigella* clone are Hg and kanamycin resistant. They are allowed to grow for many generations in the absence of IPTG. The cultures are then screened. for the presence of Hg-resistant kanamycin-sensitive clones. Three clones are isolated and further characterized. Southern blots show that they no longer hybridize with an A subunit gene internal probe but still produce high amounts of B subunit protein, as detected by monoclonal antibody analysis, and they no longer are cytotoxic.

Using the same procedure, this ToxA$^-$ clone is genetically engineered by in vitro mutagenesis of its operon coding for enterochelin. The suicide plasmid vector, that is utilized, contains the enterochelin operon of *E. coli* (66), with each of its ent F, Fep E, Fep C and Fep D subunit genes having a significant deletion at a restriction site, into which is inserted a fragment that codes for resistance to arsenite (62) and a suitable promoter for the arsenite-resistance gene. The resulting clone is Tox A$^-$ and Ent$^-$.

Using the same procedure, this Tox A$^-$ and Ent$^-$ clone is genetically engineered by in vitro mutagenesis of its ics A gene. The suicide plasmid vector, used, contains the ics A gene of *S. flexneri* (60, 61), that has a significant deletion at a restriction site, into which is inserted a fragment coding for resistance to cadmium (63, 64) and a suitable promoter for the cadmium-resistance gene. The resulting Tox A$^-$, Ent$^-$, ics A$^-$ *S. dysenteriae* 1 clone is characterized by a substantially reduced invasiveness, which renders it suitable for making a vaccine for humans against *S. dysenteriae* 1.

It is believed that this invention and many of its attendant advantages will be understood from its description above, and it will be apparent that various modifications can be made in the method and vaccine described above without departing from the spirit and scope of the invention or sacrificing all of its material advantages, the embodiments described above being merely preferred embodiments.

The references, referred to above, are as follows.

REFERENCES

1. Bridgewater, F. A. I., R. S. Morgan, K. E. K. Rowson, and G. P. Wright. 1955. the neurotoxin of *Shigella shigae*. Morphological and functional lesions produced in the central nervous system of rabbits. *Br. J. Exp. Pathol.* 36: 447.
2. Cavanagh, J. B., J. G. Howard, and J. L. Whitby. 1956. The neurotoxin of *Shigella shigae*. A comparative study of the effects produced in various laboratory animals. *Br. J. Exp. Med.* 37:272.
3. Chambers, D. E., D. A. Parks, G. Patterson, R. Roy, J. K. McCord, S. Yoshida, L. F. Parmley, and J. M. Downey. 1985. Xanthine-oxydase as a source of free radical damage in myocardial ischemia. *J. Mol. Cell. Cardiol.* 17:145.
4. Clerc, P., A. Ryter, J. Mounier, and P. J. Sansonetti. 1987. Plasmid-mediated early killing of eucaryotic cells by *Shigella flexneri* as studied by infection of J774 macrophages. *Infect. Immun.* 55:521.
5. Clerc, P., and P. J. Sansonetti. 1987. Entry of *Shigella flexneri* into HeLa cells: Evidence for directed phagocytosis involving actin polymerization and myosin accumulation. *Infect. Immun.* 55:2681.
6. Conradi, H., 1903. Ueber löshlishe, durch aseptische Autolyse, erhaltene Giftstoffe von Ruhr-un Typhus bazillen. *Dtsch. Med. Wochenschr.* 29:26.
7. Dupont, H. L., and L. K., Pickering. 1980. Bacillary dysentery, p. 61–82. In W. B. Greenough III and T. C. Merigan (ed.), infections of the Gastrointestinal tract. Current Topics in Infectious Diseases, Plenum Medical Book Company, New York.
8. Formal, S. B., P. Gemski, Jr., L. S. Baron, and E. H. Labrec. 1971. A chromosomal locus which controls the ability of *Shigella flexneri* to evoke keratoconjunctivitis. *Infect. Immun.* 3:73.
9. Formal, S. B., T. L. Hale, and P. J. Sansonetti. 1983. Invasive eoterie pathogens. *Rev. Infect. Dis.* 5:S702.
10. Gentry, M. K., and J. M. Dalrymple. 1980. Quantitative microtiter cytotoxicity assay for *Shigella* toxin. *J. clin. Microbiol.* 12:361.
11. Gianantonio, C., M. Vitacco, F. Mendilaharzu, A. Rutty, and J. Mendilaharzu. 1964. The hemolytic-uremic syndrome. *J. Pediatr.* 64:478.
12. Hale, T. L., and S. B. Formal. 1980. Cytotoxicity of *Shigella dysenteriae* 1 for cultured mammalian cells. *Am. J. Clin. Nutr.* 33:2485.
13. Huynh, T. V., R. A. Young, and R. W. Davis. 1984. DNA cloning techniques: a pratical approach. D. Glover (ed.), IRL Press, Oxford. p. 50.
14. Jackson, M. P., J. W. Newland, R. K. Holmes, and A. D. O'Brien. 1987. Nucleotide sequence analysis of the structural genes for Shiga-like toxinI encoded by bacteriophage 933J from *Escherichia coli*. *Microbial Pathogenesis* 2:147.
15. Kavi, J., J. Chant, M. Maris, and P. E. Rose. 1987. Cytopathic effect of verotoxin on endothelial cells. *Lancet* i:1035.
16. Keusch, G. T., C. F. Grady, L. J., Mata, and J. McIver. 1972. The pathogenesis of *Shigella* diarrhea. I. Enterotoxin production by *Shigella dysenteriae*. *J. Clin. Invest.* 51:1212.
17. Keusch, G. T., and M. Jacewicz. 1975. The pathogenesis of *Shigella* diarrhea. V. Relationship of Shiga enterotoxin and cytotoxio. *J. Infect. Dis.* 131:533.
18. Keusch, G. T., M. Jacewicz, M. M. Levine, R. B. Hornick, and S. Kochna. 1976. Pathogenesis of *Shigella* diarrhea. Serum anticytotoxin antibody response produced by toxigenic and neutoxigenic *Shigella dysenteriae* 1. *J. Clin. Invest.* 57:194.
19. Keusch, G. T., and M. Jacewicz. 1977. The pathogenesis of *Shigella* diarrhea. VI. Toxin and antitoxin in *Shigella flexneri* and *Shigella sonnei* infections in humans. *J. Infect. Dis.* 135:552.
20. Kinsey, M. D., S. B. Formal, G. J. Dammin, and R. A. Giannella. 1976. Fluid and electrolyte transport in Rhesus monkeys challenged intrecescelly with *Shigella flexneri* 2a. *Infect. Immun.* 14:368.
21. Kolter, R., M. Inuzuka, and D. R. Jelinski. 1978. Transcomplementetion-dependent replication of a low molecular weight origin fragment from plasmid R6K. *Cell.* 15:1199.
22. Koster, F., J. Levin, L. Walker, K. S. K. Tung, R. H. Gilman, M. M. Rajaman, M. A. Majid, S. Islam, and R. C. Williams Jr. 1977. Hemolyticuremic syndrome after shigellosis. Relation to endotoxin and circulating immune complexes. *N. Engl. J. Med.* 298:927.
23. Labrec, E. H., B. Schneider, T. J. Magnani, and S. B. Formal. 1964. Epithelial cell penetration as an essential step in the pathogenesis of bacillary dysentery. *J. Becteriol.* 88:1503.
24. Lawlor, K. M., P. A. Deskaleros, R. E. Robinson, and S. M. Payne. 1987. Virulence of iron transport mutants of *Shigella flexneri* and utilization of host iron compounds. *Infect. Immun.* 55:594.
25. Levine, M. M., H. L. DuPont, S. D. Formal, R. B. Hornick, A. Takeuchi, E. J. Gangarosa, M. J. Snyder, and J. P. Libonati. 1973. Pathogenesis of *Shigella dysenteriae* 1 (Shiga) dysentery. *J. Infect. Dis.* 127:261.
26. Maurelli, A. T., B. Blackmon, and R. Curtis III. 1984. Loss of pigmentation in *Shigella flexneri* 2a is correlated with loss of virulence and virulence-associated plasmid. *Infect. Immun.* 43:397.
27. Moyer, M. P., P. S. Dixon, S. W. Rothman, and J. E. Brown. 1987. Cytotoxicity of Shiga toxin for human colonic and ileal epithelial cells. *Infect. Immun.* 55:1533.
28. Nassif, X., M. C. Mazert, J. Mounier, and P. J. Sansonetti. 1987. Evaluation with an iuc::TnlO mutant of the role of aerobactin production in the virulence of *Shigella flexneri*. *Infect. Immun.* 55:1963.
29. Newland, J. W., N. A. Strockbine, S. F. Miller, A. D. O'Brien, and R. K. Holmes. 1985. Structural genes from a toxin converting phage of *E. coli. Science*, 230:170.
30. O'Brien, A. D., M. R. Thompson, P. Gemski, B. P. Doctor, and S. B. Formal. 1977. Biological properties of *Shigella flexneri* 2 A toxin and its serological relationship to *Shigella dysenteriae* 1 toxin. *Infect. Immun.* 15:796.
31. O'Brien, A. D., T. A. Lively, M. E. Chen, S. W. Rothman. and S. B. Formal. 1983. *Escherichia coli* 0157:H7 strains associated with haemorrhagic colitis in the United States produce a *Shigella dysenteriae* 1 (Shiga) like cytotoxin. *Lancet*, i:702.
32. O'Brien, A. D., and R. K. Holmes. 1987. Shiga and Shiga-like toxins. *Microbiol. Rev.* 51:206.
33. Olsnes, S., and K. Eiklid. 1980. Isolation and characterization of *Shigella* Shiga cytotoxin. *J. Biol. Chem.* 255:284.
34. Pai, C. H., R. Gordon, H. V. Sims, and L. E. Bryan. 1984. Sporadic cases of hemorrhagic colitis associated with *Escherichia coli* 0157: H7. Clinical, epidemiologic, and bacteriologic features. *Ann. Intern. Med.* 101:738.
35. Piéchaud, M., S. Szturm-Rubinstein, and D. Piéchaud. 1958. Evolution histologique de la kératoconjonctivite à bacilles dysentériques du cobaye. *Ann. Inst. Pasteur* 94:298.
36. Prado, D., T. C., Cleary, L. K. Pickering, C. D. Ericsson, A. V. Bartlett III, H. L. DuPont, and P. C. Johnson. 1986. The relation between production of cytotoxins and clinical features in shigellosis. *J. Infect. Dis.* 154:149.
37. Prentki, P., and M. M. Kirsch. 1984. In vitro insertional mutagenesis with a selectable DNA fragment. *Gene*, 29:303.
38. Raghupathy, P., A. Date. J. C. M. Shastry, A. Sudarsanam, and M. Jadhav. 1978. Haemolytic-uremic syndrome complicating *Shigella* dysentery in south Indian children. *Br. Med. J.* 1:1518.
39. Rigby, P. W. J., M. Dieckmann, C. Rhodes, and P. Berg. 1977. Labeling DNA to high specific activity in vitro by nick translation with DNA polymerase I. *J. Mol. Biol.* 113:237.
40. Riley, L. W., R. S. Remis, S. D. Helgerson, H. B. McGee, J. G. Wells, B. R. Davis, R. J. Hebert, E. S. Olcott, L. M. Johnson, N. T. Hagrett, P. A. Blake, and M. L. Cohen.

1983. Hemorrhagic colitis associated with a rare *Escherichia coli* serotype. *N. Engl. J. Med.* 308:681.

41. Rout, W. R., S. B. Formal, R. A. Giannella, and G. J. Dammin. 1975. The pathophysiology of *Shigella* diarrhea in the Rhesus monkey; intestinal transport, morphology and bacteriological studies. *Gastroenterology* 68:270.

42. Sansonetti, P. J., D. J. Kopecko, and S. B. Formal. 1981. *Shigella sonnei* plasmids: evidence that a large plasmid is neceessary for virulence. *Infect. Immun.* 34:75.

43. Sansonetti, P. J., D. J. Kopecko, and S. B. Formal. 1982. Involvement of a plasmid in the invasive ability of *Shigella flexneri*. *Infect. Immun.* 35:852.

44. Sansonetti, P. J., T. L. Hale, G. I. Dammin, C. Kapper, H. H. Collins Jr., and S. B. Formal. 1983. Alterations in the pathogenesis of *Escherichia coli* K12 after transfer of plasmids and chromosomal genes from *Shigella flexneri*. *Infect. Immun.* 39:1392.

45. Sansonetti, P. J., H. d'Hauteville, C. Ecobichon, and C. Pourcel. 1983. Molecular comparison of virulence plasmids in *Shigella* and enteroinvasive *Escherichia coli*. *Ann. Microbiol. (Inst. Pasteur)*, 134 A:295.

46. Sansonetti, P. J., A. Ryter, P. Clerc, A. T. Maurelli, and J. Mounier. 1986. Multiplication of *Shigella flexneri* within HeLa cells: lysis of the phagocytic vacuole and plasmid-mediated contact hemolysis. *Infect. Immun.* 51:461.

47 Sansonetti, P. J., and J. Mounier. 1987. Metabolic events mediating early killing of host cells by *Shigella flexneri*. *Microbial Patbogenesis*, 3:53.

48. Sekizaki, T., S. Harayama, G. M. Brazil, and K. N. Timmis. 1987. Localization of stx, a determinant essential for high level production of Shiga-toxin by *Shigella dysenteriae* 1, near pyrF and generation of stx transposon mutants. *Infect. Immun.* 55:2208.

49. Sereny, B. 1957. Experimental keratoconjunctivitis shigellosa. *Acts Microbiol. Acad. Sci. Hung.* 4:367.

50. Silhavy, T. J., M. M. Berman, and L. W. Enquist. 1984. DNA extraction from bacterial cells. In experiments in gene fusion. Cold Spring Harbor Laboratory, p. 137.

51. Simon, R., U. Priefer, and A. Pühler. 1983. A broad host range mobilization system for in vivo genetic engineering: transposon mutagenesis in Gram negative bacteria. *Biotechnology*, 1:784.

52. Snyderman, R., M. C. Pike, D. G. Fischer, and H. S. Koren. 1977. Biologic and biochemical activities of continuous macrophage cell lines P338 D1 and J774.1. *J. Immunol.* 119:2060.

53. Southern, E. M. 1975. Detection of specific sequences among DNA fragments separated by gel electrophoresis. *J. Mol. Biol.* 98:503.

54. Strockbine, N. A., L. R. M. Marques, R. K. Holmes, and A. D. O'Brien. 1985. Characterization of monoclonal antibodies against Shiga-like toxin from *Escherichia coli*. *Infect. Immun.* 50:695.

55. Takeuchi, A., H. Spring, E. H. LaBrec, and S. B. Formal. 1965. Experimental acute colitis in the Rhesus monkey following peroral infection with *Shigella flexneri*. *Am. J. Pathol.* 52:503.

56. Takeuchi, A. 1967. Electron microscope studies of experimental *Salmonella* infection. I. Penetration into cells of the intestinal epithelium by *Salmonella typhimurium*. *Am. J. Pathol.* 47:1011.

57. Timmis, K. N. S. Sturm, and H. Watanabe. Genetic dissection of pathogenesis determinants of *Shigella* and enteroinvasive *Escherichia coli*. In Development of Vaccines and Drugs against Diarrhea. (J. Holmgren, A. Lindberg, and R. Möllby Eds.) 11th Nobel Conf. Stockholm, 1985, p. 107–126.

58. Vieira, J., and J. Messing. 1982. The pUC plasmids, an Mβmp7 derived system for insertion mutagenesis and sequencing with synthetic universal primiers. *Gene*, 19:259.

59. Young, R. A., and R. W. Davis. 1983. Yeast RNA polymerase II gene: Isolation with antibody probes. *Science*, 222:778.

60. Bernardini et al. 1989. Identification of icsA, a plasmid locus of *Shigella flexneri* that governs bacterial intra- and intercellular spread through interaction with F-actin. *Proc. Natl. Acad. Sci. USA*. 86: 3867–3871.

61. Lett et al. 1989. Identification of the virG protein and determination of the complete coding sequence: A plasmid-coded virulence gene of *Shigella flexneri*. *J. of Bacteriology*. 171: 353–359.

62. Mobley and Summers. 1987. Plasmid-encoded ion tranport systems. *Ion Transport in Prokaryotes*. Academic Press, Inc. 305–326.

63. Nies and Silver. 1989. Plasmid-determined inducible efflux is responsible for resistance to cadmium, zinc and cobalt in *Alcaligenes eutrophus*. *J. of Bacteriology*. 171 (2): 896–900.

64. Nucifora et al. 1989. Cadmium resistance from *Staphylococcus aureus* plasmid pI258 cadA gene results from a cadmium-efflux ATPase. *Proc. Natl. Acad. Sci. USA*. 86.

65. Barrineau et al. 1984. *J. of Molec. And Appl. Genetics*. 2.601–619.

66. Ozenberger et al. 1987. Genetic organization of multiple fep genes encoding ferric enterobactin transport functions in *E. coli*. *J. of Bacteriology*. 169(8): 3638–3646.

TABLE 1

Strains, plasmids, phages and their relevant characteristics

| Strain | Species | Genotype | Plasmid/phage | Relevant characteristics |
|---|---|---|---|---|
| SC 500 | *S. dysentariae* 1 | thi, nad, trp, met | pHS7200 | Invasion of HeLa cells |
| SC 501 | *S. dysenteriae* 1 | thi, nad, trp, met, tox, spc$^r$ | pHS7200 | Invasion of HeLa cells |
| SC 502 | *S. dysentariae* 1 | thi, nad, trp, met | — | — |
| SC 503 | *S. dysenteriae* 1 | thi, nad, trp, met, tox, spc$^r$ | — | — |
| Y 1089 | *E. coli* | ΔlacU169 proA$^+$ Δlon araD139 strA hfl Δl50[chr::Tn10] | pHC9 | Ap$^r$, pBR322-lac i$^q$ |
| | | | λGT11 | lac5Δ(shindIIIλ2–3) srIλ3$^\Phi$ cI857 arIλ4' nin5 arIλ5$^\alpha$ sam100 |

TABLE 1-continued

Strains, plasmids, phages and their relevant characteristics

| Strain | Species | Genotype | Plasmid/phage | Relevant characteristics |
|---|---|---|---|---|
| Y 1090 | E. coli | ΔlacU169 proA+ Δlon araD139 strA supF[trpC22::Tn10] | pHC9 | $Ap^r$, pBR322-lac $i^q$ |
| JM 83 | E. coli | F−, araΔlac-pro strA thi, phi80dlacZ AM15 | pUC8 | $Ap^r$, cloning vehicle |
| | | | pHS7201 | $Ap^r$, Shiga toxin genes subcloned in pUC8 |
| | | | pHS7202 | $Ap^r$ $Spc^r$ Ω is inserted at the HpaI site of pHS6001 |
| | | | pHP45 | $Ap^r$ $Spe^r$ contains the Ω element |
| SM10λpir | E. coli | recA, RP4-2 TC::Mu $Km^r$ thi, thr, leu, suIII | λpir | contains the pir function from R6K replication origin |
| | | | pJM703-1 | Suicide cloning vector $Ap^r$, can be mobilized in SM10λpir |
| | | | pHS7203 | Mutagenized toxin genes cloned in pJM703-1 $Ap^r$ $Sp^r$ |
| HB101 | E. coli | $RB^-$, $MB^-$, recA, supE44 (su2)lacY, leuB6, proA2 thi-1 $Sm^r$ | — | — |

The invention claimed is:

1. A method for modifying a wild strain of an enteroinvasive *Shigella* to produce a modified strain of *Shigella* that can not spread substantially within infected cells of a host and can not spread substantially from infected to uninfected cells of the host, for use in making a vaccine against the wild strain of *Shigella*, the method comprising inactivating an icsA gene of the wild strain of *Shigella*, other than only by inactivation by means of a transposon inserted into the gene, to thereby provide a modified strain of *Shigella* that can not spread substantially within infected cells of the host and can not spread substantially from infected to uninfected cells of the host.

2. The method of claim 1, wherein the modified strain of *Shigella* also can not substantially invade cells of the host, the method further comprising inactivating an aerobactin or enterochelin gene of the wild strain of *Shigella*, other than only by inactivation by means of a transposon inserted into the gene, to thereby provide a modified strain of *Shigella* that can not spread substantially within infected cells of the host, can not spread substantially from infected to uninfected cells of the host, and can not substantially invade cells of the host.

3. The method of claim 2, wherein the modified strain of *Shigella* also can not produce toxins that kill a substantial number of the host's cells, the method further comprising inactivating a Shiga-toxin gene of the wild strain of *Shigella*, other than only by inactivation by means of a transposon inserted into the gene, to thereby provide a modified strain of *Shigella* that can not spread substantially within infected cells of the host, can not spread substantially from infected to uninfected cells of the host, can not substantially invade cells of the host, and can not produce toxins that kill a substantial number of the host's cells.

4. The method of any of claims 1–3, wherein said *Shigella* is *S. flexneri.*

5. The method of any of claims 1–3, wherein said *Shigella* is *S. dysenteriae* 1.

6. The method of claim 5, wherein one or more of the ent F, Fep E, Fep C, and Fep D subunit genes of the enterochelin operon of *S. dysenteriae* 1 are modified.

7. The method of claim 3, wherein the Shiga-toxin gene is the Shiga-toxin A gene.

8. The method of any of claims 1–3, wherein one or more of said inactivated genes are inactivated genes from which at least one nucleotide sequence has been deleted.

9. The method of any of claims 1–3, wherein one or more of said inactivated genes are inactivated genes into which at least one nucleotide sequence has been inserted.

10. The method of claim 9, wherein a marker gene is inserted into one or more of said inactivated genes.

11. The method of claim 3, further comprising isolating said modified strain of *Shigella* from said wild strain of *Shigella*.

12. A modified *Shigella* for use in making a vaccine against a wild strain of *Shigella*, the modified *Shigella* comprising:

(a) an inactivated icsA gene, inactivated other than only by means of a transposon inserted into the gene; and (b) an inactivated aerobactin or enterochelin gene, inactivated other than only by means of a transposon inserted into the gene;

wherein the modified *Shigella* can not spread substantially within infected cells of the host, can not spread substantially from infected to uninfected cells of the host, and can not substantially invade cells of the host.

13. The *Shigella* of claim 12, further comprising an inactivated Shiga-toxin gene, inactivated other than only by means of a transposon inserted into the gene;

wherein the modified *Shigella* can not spread substantially within infected cells of the host, can not spread substantially from infected to uninfected cells of the host, can not substantially invade cells of the host, and can not produce toxins that kill a substantial number of the host's cells.

14. The *Shigella* of claim 13, wherein the Shiga-toxin gene is Shiga-toxin A.

15. The *Shigella* of claim 12 or 13, wherein said *Shigella* is *S. dysenteriae* 1 or *S. flexneri*.

16. The *Shigella* of claim 12 or 13, comprising inactivated ent F, Fep E, Fep C, or Fep D subunit genes of the enterochelin operon.

17. The *Shigella* of claim 12 or 13, wherein one or more of said inactivated genes are inactivated genes from which at least one nucleotide sequence has been deleted.

18. The *Shigella* of claim 12 or 13 wherein one or more of said inactivated genes are inactivated genes into which at least one nucleotide sequence has been inserted.

19. The *Shigella* of claim 18 wherein a marker gene is inserted into one or more of said inactivated genes.

20. A vaccine comprising the *Shigella* of claim 12 or 13 and a pharmaceutically acceptable vehicle.

21. The method of any of claims 1–3, wherein a marker gene is inserted into each inactivated gene.

22. The *Shigella* of claim 12 or 13, wherein a marker gene is inserted into each inactivated gene.

23. A vaccine comprising the *Shigella* of claim 22 and a pharmaceutically acceptable vehicle.

24. The method of claim 1, wherein said inactivation of said icsA gene comprises allelic exchange with a mutagenized icsA gene that has been mutagenized in vitro.

25. The method of claim 2, wherein said inactivation of said icsA gene comprises allelic exchange with a mutagenized icsA gene that has been mutagenized in vitro, and wherein said inactivation of said aerobactin or enterochelin gene comprises allelic exchange with a mutagenized aerobactin or enterochelin gene that has been mutagenized in vitro.

26. The method of claim 3, wherein said inactivation of said icsA gene comprises allelic exchange with a mutagenized icsA gene that has been mutagenized in vitro, wherein said inactivation of said aerobactin or enterochelin gene comprises allelic exchange with a mutagenized aerobactin or enterochelin gene that has been mutagenized in vitro, and wherein said inactivation of said Shiga-toxin gene comprises allelic exchange with a mutagenized Shiga-toxin gene that has been mutagenized in vitro.

27. The method of any of claims 24–26, wherein a marker gene is inserted into one or more of said mutagenized genes.

28. A modified *Shigella* for use in making a vaccine against a wild strain of *Shigella*, the modified *Shigella* comprising:
(a) an inactivated icsA gene, inactivated by allelic exchange with a mutagenized icsA gene that has been mutagenized in vitro, wherein said mutagenesis is other than only by means of a transposon inserted into the gene; and
(b) an inactivated aerobactin or enterochelin gene, inactivated by allelic exchange with a mutagenized aerobactin or enterochelin gene that has been mutagenized in vitro, wherein said mutagenesis is other than only by means of a transposon inserted into the gene;
wherein the modified *Shigella* can not spread substantially within infected cells of the host, can not spread substantially from infected to uninfected cells of the host, and can not substantially invade cells of the host.

29. The *Shigella* of claim 28, further comprising an inactivated Shiga-toxin gene, inactivated by allelic exchange with a mutagenized Shiga-toxin gene that has been mutagenized in vitro, wherein said mutagenesis is other than only by means of a transposon inserted into the gene;
wherein the modified *Shigella* can not spread substantially within infected cells of the host, can not spread substantially from infected to uninfected cells of the host, can not substantially invade cells of the host, and can not produce toxins that kill a substantial number of the host's cells.

30. The *Shigella* of claim 28 or 29, wherein a marker gene is inserted into one or more of said mutagenized genes.

31. A vaccine comprising the *Shigella* of claim 28 or 29 and a pharmaceutically acceptable vehicle.

32. A modified *Shigella* for use in making a vaccine against a wild strain of *Shigella*, the modified *Shigella* comprising an inactivated icsA gene, inactivated other than only by means of a transposon inserted into the gene;
wherein the modified *Shigella* can not spread substantially within infected cells of the host and can not spread substantially from infected to uninfected cells of the host.

33. The *Shigella* of claim 32, wherein at least one nucleotide sequence has been deleted from said inactivated icsA gene.

34. The *Shigella* of claim 32, wherein at least one nucleotide sequence has been inserted into said inactivated icsA gene.

35. The *Shigella* of claim 34, wherein a marker gene is inserted into said inactivated icsA gene.

36. A vaccine comprising the *Shigella* of claim 32 and a pharmaceutically acceptable vehicle.

37. A modified *Shigella* for use in making a vaccine against a wild strain of *Shigella*, the modified *Shigella* comprising an inactivated icsA gene, inactivated by allelic exchange with a mutagenized icsA gene that has been mutagenized in vitro, wherein said mutagenesis is other than only by means of a transposon inserted into the gene;
wherein the modified *Shigella* can not spread substantially within infected cells of the host and can not spread substantially from infected to uninfected cells of the host.

38. The *Shigella* of claim 37, wherein a marker gene is inserted into said mutagenized icsA gene.

39. A vaccine comprising the *Shigella* of claim 37 and a pharmaceutically acceptable vehicle.

* * * * *